United States Patent
Henco et al.

(10) Patent No.: US 6,213,735 B1
(45) Date of Patent: Apr. 10, 2001

(54) MICROMECHANICAL EJECTION PUMP FOR SEPARATING SMALL FLUID VOLUMES FROM A FLOWING SAMPLE FLUID

(75) Inventors: Karsten Henco, Erkrath; Rolf Guenther, Hamburg; Steffen Howitz, Dresden; Thomas Wegener, Neuruppin, all of (DE)

(73) Assignee: Evotec Biosystem AG, Hamburg (DE)

( * ) Notice: Subject to any disclaimer, the term of this patent is extended or adjusted under 35 U.S.C. 154(b) by 0 days.

(21) Appl. No.: 09/308,705
(22) PCT Filed: Nov. 22, 1997
(86) PCT No.: PCT/EP97/06543
  § 371 Date: Dec. 21, 1999
  § 102(e) Date: Dec. 21, 1999
(87) PCT Pub. No.: WO98/23276
  PCT Pub. Date: Jun. 4, 1998

(30) Foreign Application Priority Data

Nov. 22, 1996 (DE) .............................. 196 48 458

(51) Int. Cl.[7] .................................................. F04B 17/00
(52) U.S. Cl. ............................................. 417/413.2
(58) Field of Search ........................... 417/317, 413.2, 417/413.3, 322; 604/67, 131; 204/1.11; 435/287.2; 128/203.12; 436/180

(56) References Cited

U.S. PATENT DOCUMENTS

| | | | |
|---|---|---|---|
| 4,024,544 | | 5/1977 | Vernon ...................................... 346/1 |
| 4,344,743 | * | 8/1982 | Bessman et al. .................... 417/317 |
| 4,614,953 | | 9/1986 | Lapeyre ............................. 346/140 R |
| 5,205,819 | * | 4/1993 | Ross et al. .............................. 604/67 |
| 5,336,062 | * | 8/1994 | Richter ................................ 417/413.2 |
| 5,472,577 | * | 12/1995 | Porter et al. .......................... 204/1.11 |
| 5,529,465 | * | 6/1996 | Zengerle et al. .................. 417/413.2 |
| 5,693,016 | * | 12/1997 | Gumaste et al. ..................... 604/131 |
| 5,759,014 | * | 6/1998 | Lintel ................................. 417/413.3 |
| 5,922,591 | * | 7/1999 | Anderson et al. ................. 435/287.2 |
| 5,961,298 | * | 10/1999 | Bar-Cohen et al. .................. 417/322 |
| 6,010,316 | * | 1/2000 | Haller et al. .......................... 417/322 |
| 6,032,665 | * | 3/2000 | Psaros ............................. 128/203.12 |
| 6,083,762 | * | 7/2000 | Papen et al. .......................... 436/180 |
| 6,116,863 | * | 9/2000 | Ahn et al. ............................. 417/322 |

FOREIGN PATENT DOCUMENTS

| | | |
|---|---|---|
| 0 356 160 | 2/1990 | (EP) . |
| 0 538 147 | 4/1993 | (EP) . |
| 0 668 500 | 8/1995 | (EP) . |
| 2 306 644 | 9/1996 | (GB) . |
| WO 96/04547 | 2/1996 | (WO) . |
| WO 97/01085 | 1/1997 | (WO) . |

OTHER PUBLICATIONS

Nilsson et al., *J. Biochemical and Biophysical Methods*, 27 (1993), pp. 181–190.
Wallman et al., *Transducers 95. Eurosensors IX*, Jun. 25–29, 1995, Stockholm.

* cited by examiner

*Primary Examiner*—Teresa Walberg
*Assistant Examiner*—Leonid Fastovsky
(74) *Attorney, Agent, or Firm*—Fish & Richardson P.C., P.A.

(57) ABSTRACT

A micromechanical ejection pump for extracting small fluid volumes from a flowing sample fluid is provided with a substrate, and a canal for pressurized working fluid. The micromechanical ejection pump also has a canal for ejecting a fluid volume from the sample fluid. The working fluid canal runs into the extension of the sample fluid canal discharging crosswise thereto. The ejection canal connected to the sample fluid canal branches off from the working fluid canal opposite to the sample fluid canal. The working fluid canal and the ejection canal have in particular a substantially similar cross-section of 0.01–0.12 mm$^2$, wherein the ratio of the cross-section of the sample fluid canal to the cross-section of the working fluid canal or the ejection canal is preferably between 0.2 and 0.5, more particularly between 0.3 and 0.4 and most preferably 0.35.

16 Claims, 1 Drawing Sheet

MICROMECHANICAL EJECTION PUMP FOR SEPARATING SMALL FLUID VOLUMES FROM A FLOWING SAMPLE FLUID

TECHNICAL FIELD

The present invention relates to a micromechanical ejection pump for separating small fluid volumes from a flowing sample fluid, by means of which sample fractions can be physically separated from a continuous sample flow with very small dead volumes occurring during this process.

BACKGROUND

The separation of small fluid volumes from a fluid flow poses relevant problems in many areas of chemical, biological and pharmaceutical analytics. It is frequently desirable to feed macromolecules, which have already been high-dissolution separated by a chromatographic process and are available as a fluid sample, directly to an analysis system, such as a gel electrophoresis. Devices have been described which allow such fluid dosing. According to Nilsson et al. (Journal of Biochemical and Biophysical Methods 27, 181–190 (1993)) such a device comprises a water-filled pumping chamber with attached piezoceramics. Upstream of the pumping chamber discharge a brass block is arranged through which a steel cannula is guided. This steel cannula carrying the sample flow possesses two openings arranged at right angles to the flow axis, one of which serves as connection for the pumping chamber and the other one for ejection of the microdroplets to be selected. To avoid mixing effects the fluid flow and the pumping chamber fluid are separated by a Teflon membrane of small thickness via which the pressure wave required for droplet formation can propagate. Coupling of the sample chamber to the pumping chamber is effected here by means of four bolts. The volume of the sample chamber proper is 5 $\mu$l. The overall volume of the device is indicated as 34 $\mu$l. This device is disadvantageous because of the complicated manufacturing technology and the relatively large volume.

Wallman et al. (Proc. Transducer 95, 303–304) describe a device in which the sample chamber is of sandwich configuration. Here two silicon wafers, into which 2 mm×15 mm×350 $\mu$l large cavities have been etched, are interconnected thus building a flow duct. The upper wafer presents a hole at each end of the sample chamber, which allows inflow and outflow of the sample fluid. Between the holes a piezoceramics is arranged which allows sample ejection through an oppositely arranged 60 $\mu$m diameter hole in the lower wafer. The dead volume of this device amounts to approximately 1 $\mu$l.

The microfluid manipulator described in EP 0 672 834 is a device with two functional units, a microdroplet emitter and a microfluid diode. Dosing fluid droplets are injected by means of a microdroplet emitter into a droplet chamber where they wet the input surface of the microfluid diode which allows feeding the fluid medium into a target fluid. The overall volume of the microdroplet emitter and the supply duct amounts to approximately 1 $\mu$l. Another disadvantage presented by this device is that thorough mixing of the fluid to be dosed in may occur in the microdroplet emitter.

SUMMARY

The object underlying the present invention is to reduce the volume of the dosing device and to allow dosing of a very small sample fraction without any mixing effects. The manufacturing process for such miniaturized device should involve very small manufacturing efforts.

The micromechanical ejection pump according to the invention is in particular integrated in a substrate and is in particular manufactured by injection molding or micromechanical treatment (e.g. etching in an etchable substrate material). In the substrate a sample fluid duct is formed which is intersected by a second duct. The sample fluid flows through the sample fluid duct while the working fluid passes through the working fluid duct with the working fluid preferably being inert to the sample fluid. The second duct comprises a first section connected with the first pressure/suction pump and joining the sample fluid duct in transverse direction. At the sample fluid duct side opposite this junction the second section (so-called ejection duct) of the second duct starts. Via this ejection duct that fraction of the sample fluid, which is just present between the two junctions where the working fluid duct and the ejection duct join the sample fluid duct, is ejected together with the working fluid which flows under pressure through the working fluid duct with the aim of ejecting the sample fraction.

Preferably the cross-sectional areas of the working fluid duct and the ejection duct are essentially identical and range in particular between 0.01 mm$^2$ and 0.12 mm$^2$. The ratio of the cross-sectional area of the sample fluid duct to the cross-sectional area of the working fluid duct and the ejection duct respectively ranges in particular between 0.2 and 0.5, in particular between 0.3 and 0.4 and is preferably 0.35.

BRIEF DESCRIPTION OF THE DRAWINGS

An embodiment of the invention is explained in detail with reference to the drawings.

DETAILED DESCRIPTION

Figure 1:
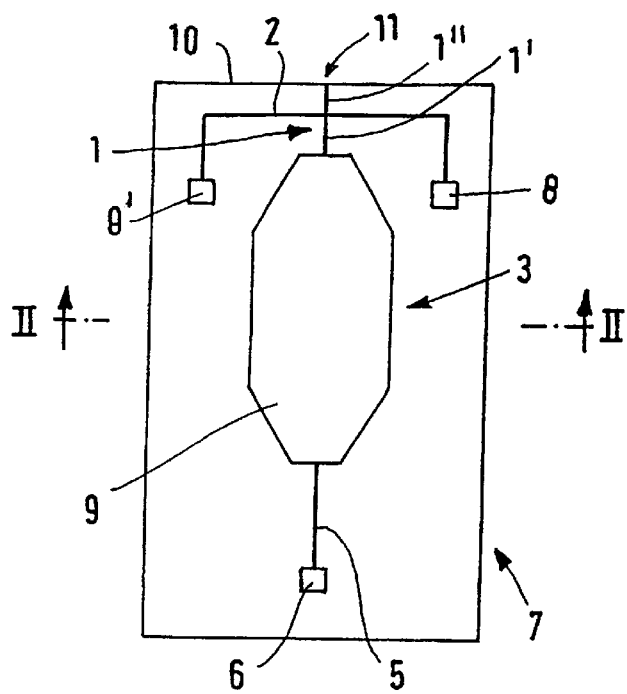
FIG. 1 shows a top view of a substrate with a sample fluid duct and working fluid and ejection ducts intersecting the sample fluid duct as well as a pressurizable pressure chamber to which working fluid is supplied via a supply duct.

In a device according to the invention as per FIG. 1, a sample fluid-carrying sample fluid duct 2 is coupled to the discharge duct 1 of a micropump 3 with the fluid being transported at right angles to the direction of ejection of the microejection pump. The discharge duct 1 joins the sample fluid duct 2 at an angle of essentially 90° and intersects it and leaves the sample fluid duct 2 at a location opposite the junction point so that the lumens of the two ducts are interconnected. Droplet generation by means of the microejection pump can in particular be realized by two different functional principles. It is possible to realize the pressure pulse required for droplet ejection via a temperature jump in a small portion of the working fluid in the microejection pump in accordance with the so-called thermal or bubble jet principle. The microejection pump can at option be operated by means of a piezoelectrical actuator. When the microejection pump is energized in accordance with the so-called droplet-on-demand principle a mixture of preferably inert working fluid and the sample fraction to be discharged is ejected. The discharge duct is connected with the pressure chamber 9 of the micropump 3. Working fluid is fed to the pressure chamber 9 via a supply duct 5 from a storage container (not shown) which can be connected with the supply duct 5 via connector 6.

By employing the duct structures according to the invention it is possible to essentially reduce the volume of the fluid structure as compared with the state of the art. Rapid change of the sample fluid and thus a higher sample flow are allowed. With the aid of the device according to the invention it is thus possible to separate fragments, such as chemical reagents or cell parts, from a sample flow. In particular minimum sample fractions, which are available as highly dissolved fractions, can be isolated without being mixed. Thanks to the direct inter-connection of the duct structures, the working fluid can also be used as flushing fluid in a most advantageous manner.

According to FIG. 1 all duct structures as well as the microejection pump are integrated in a substrate 7. The sample fluid duct comprises two connectors 8, 8' between which the duct extends in the substrate 7. The discharge duct 1 runs transversely to the sample fluid duct 2 with the discharge duct 1 comprising a first section 1' and a second section 1". The first section 1' extends from the pressure chamber 9 of the micropump 3 to the sample fluid duct 2. The second section 1" runs in extension of the first section 1' from the sample fluid duct 2 to the edge 10 of the substrate 7 where the discharge opening 11 is located. The first section 1' of the discharge duct 1 is referred to as working fluid duct since the working fluid in the pressure chamber 9 flows through this section. The working fluid plus the fraction to be ejected of the sample fluid flowing through the sample fluid duct 2 passes through the second duct section 1", the so-called ejection duct. The working fluid is fed via the supply duct 5 to the pressure chamber 9.

Dimensioning of the microstructure ducts in accordance with the invention ensures that the working fluid does not escape via the supply duct 5 but via the discharge duct 1 when pressure is applied to the working fluid, and it can be observed during the subsequent pressure-relief of the working fluid that the working fluid from the storage container is supplied via the supply duct 5 to the chamber of the micropump 3, and that working fluid, perhaps mixed with the sample fluid, is not sucked back into the chamber via the discharge duct 1 connected with the sample fluid duct 2.

In accordance with the invention the discharge duct 1 is to be preferably configured in such a way that it presents the following dimensions:

Length L: $0.6 \text{ mm} \leq L \leq 0.8 \text{ mm}$

Width W: $0.1 \text{ mm} \leq W \leq 0.15 \text{ mm}$

Depth D: $0.1 \text{ mm} \leq D \leq 0.8 \text{ mm}$

The length of the sample fluid duct 2 may be variable thus allowing suitable coupling of the device according to the invention to existing separation and analysis systems. The width W and the depth D of the sample fluid duct should be preferably selected in such a way that $0.1 \text{ mm} \leq W \leq 0.5 \text{ mm}$ and $0.04 \text{ mm} \leq D \leq 0.08 \text{ mm}$.

The length of the supply duct 5 may also be variable. The appropriate width W is $0.1 \leq W \leq 0.3$ mm. The supply duct presents in particular a depth D of $0.04 \text{ mm} \leq D \leq 0.08 \text{ mm}$.

Figure 2:
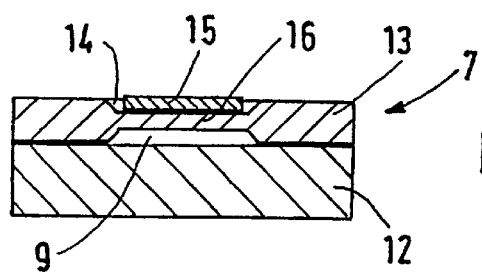
FIG. 2, shows a section across line II—II of FIG. 1

FIG. 2 shows a section through the pressure chamber along line II—II. It can be seen that the substrate 7 comprises a glass substrate 12 and a silicon wafer 13 located upon it. Cavities are etched into the lower side of the silicon wafer 13; FIG. 2 shows the cavity for the pressure chamber 9. The upper side of the silicon wafer 13 also presents a cavity 14 in which a piezo-actuator 15 is located. The silicon wafer and the glass substrate are in sealing connection with each other. The generation of the two cavities 9 and 14 produces a membrane 16 in the silicon wafer 13, which is displaced when the piezoactuator 15 is activated in order to build up pressure in the pressure chamber 9.

In a preferred embodiment the substrate comprises a wafer of a material (e.g. Si, $SiO_2$, $Si_3N_4$, GaAs) employed in micro-electronic or micromechanical devices or of plastics. The manufacture may be effected in accordance with known processes, e.g. LIGA or injection molding, with an extremely high accuracy and reproducibility. The electronic system required for evaluation of the detection signals and control of the microejection pump can in this variant preferably be monolithically integrated in the wafer. The device according to the invention may also comprise a glass/silicon layer structure with the three-dimensionally microstructured silicon body being atomically connected with a glass cover plate by anodic bonding.

Figure 3:
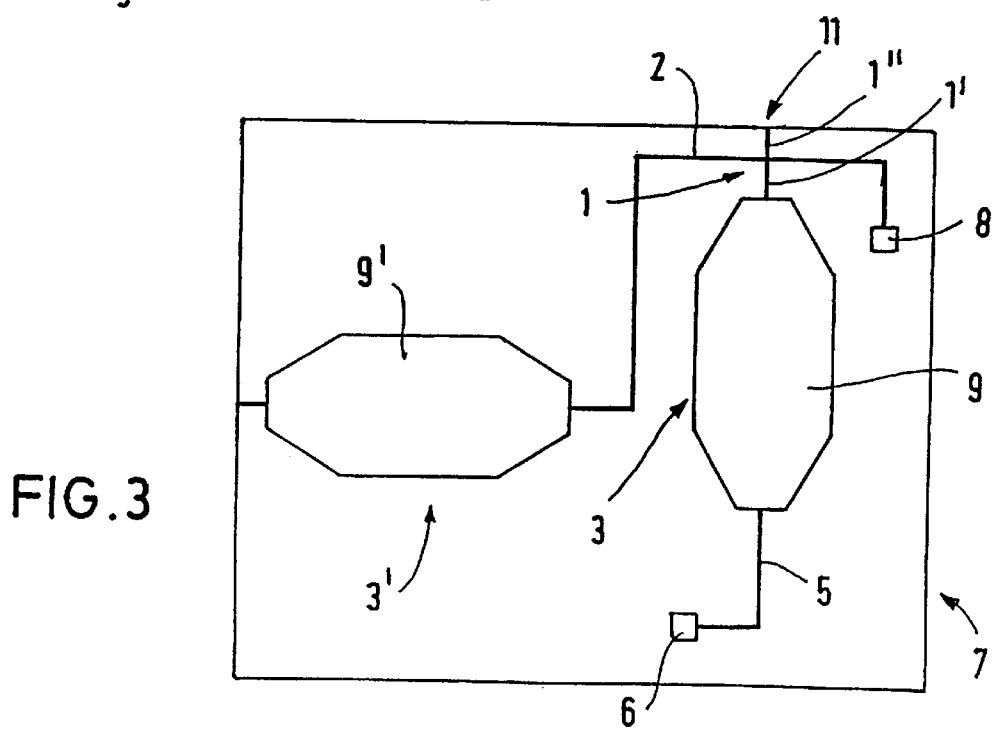
FIG. 3 shows a top view of a micromechanically treated substrate for an alternative configuration of an ejection pump with an integrated pumping chamber for the working fluid and a pumping chamber for the sample fluid.

Transport of the sample flow in the sample fluid duct 2 may be effected in a manner known to the expert using a conventional pump by pressure application at the inlet branch 8 or suction at the outlet branch 8' of the sample fluid duct 2. It is also possible to carry out the transport by means of a further micro-pump 3' integrated in the substrate. This preferred embodiment is shown in FIG. 3 where the above features and characteristics described in connection with FIGS. 1 and 2 also prevail in the embodiment as per FIG. 3.

Detection of the sample fragments to be selected may be performed by means of a sensor element which is located at a suitable distance upstream of or directly local to the inter-section of the sample fluid duct 2 with the discharge duct 1 of the micropump 3. As a particulary advantageous detection method the fluourescence correlation spectroscopy according to WO-A-94/16313 should be applied which allows functional characterisation of individual molecules or molecule complexes, viruses or individual cells. Furthermore an optical analysis system on the basis of the near-field spectroscopy according to WO-A-96/13744 may be employed. Control of the microejection pump during detection of a particular sample fragment may be effected by means of known control units.

The device according to the invention is not only used for separation of previously identified particles. It can in particular be employed as an alternative to conventional dispensing means. In such a case it may be desirable that the working fluid is identical with the sample fluid.

The device as individual element or as array structure may be part of automatic separation systems. Thus in particular several microejection pumps may be monolithically integrated on a wafer together with the associated microejection pump. It may also be desirable in certain applications to feed the sample fragments separated in compliance with the process according to the invention by means of a microfluid diode as described in EP-A-0 672 834.

On the basis of FIG. 3 an alternative configuration of the ejection pump according to the invention is described below.

As compared with the ejection pump according to FIG. 1 the alternative ejection pump as per FIG. 3 is supplemented by an integrated micropump 3' to maintain the sample fluid flow in the sample fluid duct 2. This micropump 3' comprises a pressure/suction chamber 9' integrated in the substrate 7, which is connected to the sample fluid duct 2. In all other respects the embodiment to FIG. 3 corresponds to that of FIG. 1.

The microejection pump described herein and shown in the drawing can in particular be combined with the subject matter of DE-C-195 44 127 with the multielectrode array mentioned there to control the position and/or positional change of suspended particles of the sample fluid being arranged in the sample fluid duct 2. Alternatively the sample fluid duct 2 can be provided with electrode arrays for the purpose of microparticle positioning as described in the German patent applications 196 53 659.6 and 196 53 661.3 of Dec. 20, 1996. The contents of these two patent applications as well as DE-C-195 44 127 is included in the disclosure of the present invention by reference.

What is claimed is:

1. A micromechanical ejection pump for separation of small fluid volumes from a flowing sample fluid, the pump comprising:

a substrate;

a sample fluid duct for a sample fluid formed in the substrate;

a working fluid duct for pressurizable working fluid formed in the substrate; and a supply duct via which working fluid can be supplied to the working fluid duct and an ejection duct to eject a fluid volume from the sample fluid, wherein:

the working fluid duct extends transversely to the sample fluid duct and joins the sample fluid duct, the ejection duct is connected with the sample fluid duct and branches off the sample fluid duct opposite the working fluid duct, the sample fluid duct, the working fluid duct and the ejection duct are in fluid connection with each other, and the working fluid duct, the ejection duct and the sample fluid duct have, at least in the area of the fluid connection, dimensions determining their respective cross-sections which are less than or equal to approximately one millimeter.

2. A micromechanical ejection pump according to claim 1, wherein the ratio of the cross-section of the sample fluid duct to the cross-section of the working fluid and the ejection duct respectively ranges between approximately 0.2 and 0.5.

3. A micromechanical ejection pump according to claim 1, wherein the ratio of the cross-section of the sample fluid duct to the cross-section of the working fluid and the ejection duct respectively ranges between 0.3 and 0.4.

4. A micromechanical ejection pump according to claim 1, wherein the ratio of the cross-section of the sample fluid duct to the cross-section of the working fluid and the ejection duct respectively is approximately 0.35.

5. A micromechanical ejection pump according to claim 2, wherein the working fluid duct and the ejection duct have essentially the same cross-section ranging between approximately 0.01 mm$^2$ and 0.12 mm$^2$.

6. A micromechanical ejection pump according to claim 2, wherein the sample fluid duct, the working fluid duct and the ejection duct run substantially straight in their junction and branching areas.

7. A micromechanical ejection pump according to claim 2, wherein a first pump for the working fluid connected with the working fluid duct is integrated in the substrate with the pump being arranged between the working fluid duct and the supply duct.

8. A micromechanical ejection pump according to claim 7, wherein the first pump comprises a pressure chamber with a membrane upon which a piezo-actuator acts for the purpose of pumping working fluid through the working fluid duct.

9. A micromechanical ejection pump according to claim 7, wherein a second pump for the sample fluid connected with the sample fluid duct is integrated in the substrate.

10. A micromechanical ejection pump according to claim 1, wherein the working fluid duct and the ejection duct have essentially the same cross-section ranging between 0.01 mm$^2$ and 0.12 mm$^2$.

11. A micromechanical ejection pump according to claim 1, wherein the sample fluid duct, the working fluid duct and the ejection duct run straight in their junction and branching areas.

12. A micromechanical ejection pump according to claim 11, wherein the working fluid duct and the ejection duct extend along a common straight longitudinal axis which runs transversely to the longitudinal axis of the sample fluid duct.

13. A micromechanical ejection pump according to claim 1, wherein a first pump for the working fluid connected with the working fluid duct is integrated in the substrate with the pump being arranged between the working fluid duct and the supply duct.

14. A micromechanical ejection pump according to claim 13, wherein the first pump comprises a pressure chamber with a membrane upon which a piezo-actuator acts for the purpose of pumping working fluid through the working fluid duct.

15. A micromechanical ejection pump according to claim 14, wherein a second pump for the sample fluid connected with the sample fluid duct is integrated in the substrate.

16. A micromechanical ejection pump according to claim 15, wherein the second pump comprises a pressure chamber with a membrane upon which a piezo-actuator acts for the purpose of pumping sample fluid through the sample fluid duct.

* * * * *